United States Patent [19]

Kostic et al.

[11] Patent Number: 4,857,231

[45] Date of Patent: Aug. 15, 1989

[54] THERMOCHROMIC PLATINUM COMPLEXES

[75] Inventors: Nenad M. Kostic; Xia-Ying Zhou, both of Ames, Iowa

[73] Assignee: Iowa State University Research Foundation, Inc., Ames, Iowa

[21] Appl. No.: 202,456

[22] Filed: Jun. 6, 1988

[51] Int. Cl.$^4$ .................. C07D 279/00; C07D 285/00
[52] U.S. Cl. ..................................... 252/408.1; 546/5; 252/962; 374/100
[58] Field of Search ..................... 252/408.1, 582, 583, 252/586, 962; 546/5; 374/100

[56] References Cited

U.S. PATENT DOCUMENTS

| | | | |
|---|---|---|---|
| 2,809,197 | 10/1957 | Kruse et al. | 260/270 |
| 3,929,773 | 12/1975 | Yamahara et al. | 260/242 |
| 3,935,228 | 1/1976 | Keblys | 260/270 |
| 4,151,185 | 4/1979 | Allcock et al. | 260/429 |
| 4,214,088 | 7/1980 | Abeler et al. | 546/321 |
| 4,237,301 | 12/1980 | Ghelli et al. | 546/327 |
| 4,419,515 | 12/1983 | Ghelli et al. | 546/5 |
| 4,515,954 | 5/1985 | Lang, Jr. et al. | 548/109 |
| 4,661,516 | 4/1987 | Brown et al. | 514/492 |

Primary Examiner—John F. Terapane
Assistant Examiner—Susan Wolffe
Attorney, Agent, or Firm—Zarley, McKee, Thomte, Voorhees & Sease

[57] ABSTRACT

Thermochromic compounds containing the [Pt(dipic)Cl]$^-$ anion. These compounds are yellow and monomeric at high temperatures or in low concentrations and abruptly change to red and polymeric at low temperatures or higher solution concentrations. This unusual property allows them to be used as temperature sensors.

11 Claims, No Drawings

THERMOCHROMIC PLATINUM COMPLEXES

GRANT REFERENCE

This work was financed in part by the U.S. Department of Energy, Office of Basic Energy Sciences, Chemical Sciences Division, under Contract W-7405-ENG-82. The government may have certain rights in the invention.

BACKGROUND OF THE INVENTION

In industry there are many instances where "temperature alert" signals are needed. In many cases, when a temperature reaches above or below a certain value or a set range, this change must be observed and a response made. This often occurs in operation of chemical processes, in storage of packaged temperature-sensitive products, and the like. Moreover, there are many instances where it is simply impractical to have sophisticated electrical sensors, either because such devices are too expensive or because of the skill needed for their operation and maintenance.

There is therefore a real and continuing need for the development of thermochromic materials, which can change color as the temperature changes. They are similar to the litmus paper, used for testing the acidity or basicity of solutions. Moreover, there is also a continuing need for the development of thermochromic materials whose color is responsive over a wide range of pH, regardless of the other ions present in the medium.

An ideal thermochromic material is one whose color changes abruptly, rather than gradually, so that a sudden change is immediately apparent to observers who are monitoring temperature. An ideal thermochromic material is also one whose concentration can be varied in order to adjust the threshold temperature, at which the color changes. In the ideal case, the variables affecting the temperature threshold can be controlled. Here, this "alert temperature" can be varied by simply varying the concentration.

A yet further characteristic of an ideal thermochromatic material is that it undergoes not only a color change, but also a phase change. Thus, observers who are monitoring the temperature to determine change can immediately see not only color, but also phase change. Finally, the changes in color and phase should occur suddenly and dramatically for easy notice.

The primary objective of the present invention is to provide a thermochromic material that is closer to the ideal material than those used before, in the sense that the "alert temperature" can be varied by simply manipulating the concentration of the thermochromatic material.

A yet further objective of the present invention is to provide a thermochromic material which not only has color change based upon sensing of temperature, but which also has phase change.

A still further objective of the present invention is to provide a thermochromic material which is easy to prepare, and which provides dramatic, sudden, and reversible color and phase changes.

The method and manner of accomplishing each of these objectives as well as others will become apparent from the detailed description of the invention which follows hereinafter.

SUMMARY OF THE INVENTION

This invention concerns thermochromic complexes of platinum(II), which contain the anion $[Pt(dipic)Cl]^-$. These complexes in aqueous solution are thermochromic over a wide pH range and regardless of the cations present. The variation in temperature or in concentration causes two changes, a change in color and a change in phase, which are sudden, concurrent, and reversible.

BRIEF DESCRIPTION OF THE DRAWINGS

FIG. 1 is a graph showing the characteristic thermochromism and phase change for the compounds of the present invention, and how those can be manipulated to provide an alert for different threshold temperatures.

DETAILED DESCRIPTION OF THE INVENTION

The complexes of this invention are new, never having been prepared or used before. They are thermochromic platinum(II) complexes of the formula:

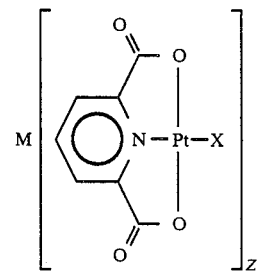

In the formula, M is a metal cation, X is a halide anion, and Z is a whole number equal to the cationic charge of M. Aqueous solutions of these complexes have been found to have the highly unusual property of being thermochromic over a wide pH range, regardless of the cation present. Moreover, the variation in temperature or in concentration causes two sudden and abrupt changes, one in color and one in phase, both of which are reversible. At lower concentrations and higher temperatures, the aqueous solution of the thermochromatic platinum(II) complexes is yellow and monomeric. However, at lower temperatures or higher concentrations there is an abrupt and sudden and reversible color change to red and phase change to a gel-like state. In particular, as the color changes to red and the phase changes to a gel-like state, the material abruptly polymerizes. Thus, at higher temperatures or lower concentrations the complex is soluble, yellow, and monomeric, whereas at lower temperatures or higher concentrations it is insoluble, red, and polymeric. As later explained, the thermochromic material is formed by a reaction involving 2,6-pyridinedicarboxylic acid, often referred to here as "dipic" for brevity. The polymeric form is gel-like, and is red in color, and is microcrystalline, and is composed of stacked $[Pt(dipic)Cl]^-$ units. Unlike other square-planar complexes that form stacks, the soluble form of $[Pt(dipic)Cl]^-$ remains monomeric over a wide range of concentration and temperature until the sudden onset of polymerization. The nucleation and growth of the polymer are easily monitored owing to the concomitant color change. The square planar platinum(II) complex undergoes sudden polymerization by stacking and the resulting gel-like polycrystalline material is red, unlike the yellow solution.

As earlier stated, the complex undergoes the changes here described regardless of the cation present; and the cation, M, may be monovalent, divalent, or trivalent. Suitable monovalent cations include lithium, sodium, potassium, cesium, and ammonium. Suitable divalent cations include magnesium, calcium, and barium. Suitable trivalent cations include aluminum and polyatomic cations of Group-V elements (nitrogen, phosphorus, arsenic) that form water-soluble salts. While any cations are satisfactory it has been found that potassium seemed to work the best and is therefore preferred. The sodium and the calcium salts did behave some atypically in yielding precipitates, rather than gel-like materials, at low temperatures.

The symbol X in the earlier presented formula represents any suitable anion, preferably a halide, but it is believed that both cyanide and thiocyanat may also work. It is preferred, however, that X be a halide and most preferred that X is chloride. Chloride has been found most suitable for the reaction in preparing the thermochromic platinum(II) complexes from the anion 2,6-pyridinedicarboxylate, i.e., "dipicolinate."

The thermochromic compounds of this invention are found to exhibit the characteristic thermochromism and phase change best in aqueous solutions; these changes also occur in solutions that are predominantly aqueous compositions. The compounds are soluble in water and the concentration in the aqueous solution can range from about 5 mM to about 200 mM, preferably from about 10 mM to about 60 mM.

FIG. 1, a phase diagram for the thermochromic compounds of the present invention, shows how both the color and the phase depend on concentration and temperature of the solution. At conditions above the line, A, the compound is soluble, yellow, and monomeric. At conditions of temperature and concentration below line B, the compound is insoluble, red, and polymeric, consisting of the stacked [Pt(dipic)Cl]$^-$ anions and the corresponding M cations. At conditions between A and B the red and yellow phases coexist. The line A marks the temperature at which the first red spots appear on cooling, whereas the line B marks the temperatures at which the last red spots disappear on heating at the solution. Since the area between the lines A and B is narrow, the changes are sudden and rapid. It can be seen from FIG. 1 that concentration of the solution can be varied to determine the threshold temperature at which the color change and phase change will occur.

The thermochromic platinum(II) complexes of the present invention may be prepared by a simple and direct reaction. In simplest description, the reaction is effected by mixing ammonium dipicolinate and potassium tetrachloroplatinate, in equimolar quantities, in an aqueous solution under mild conditions. The complex is then purified by conventional ion-exchange chromatography. The reaction which forms the thermochromic platinum(II) complex can be represented by equation (1). Various [Pt(dipic)Cl]$^-$ salts with different cations can be prepared by cation exchange or, in the case of the bulky cations, by precipitation.

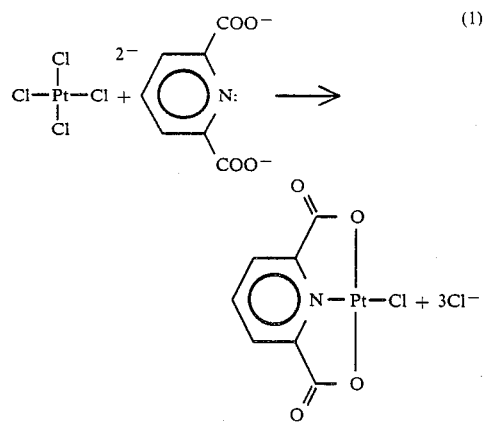

Since the acid dipicH$_2$ is sparingly soluble in water, the substitution reactions were carried out with its salts (NH$_4$)$_2$dipic and K$_2$dipic. The reaction between the anions PtCl$_4{}^{2-}$ and dipic is slow at room temperature. On heating, however, the reaction shown in eq 1 occurs readily.

Dipicolinic acid (2,6-pyridinedicarboxylic) acid is known and easily available, for example, from Sigma Chemical Company. However, as earlier explained, since it is sparingly soluble, it was converted to (NH$_4$)$_2$dipic and K$_2$dipic.

The following examples are offered to further illustrate but not limit the processes, compositions and uses of the present invention.

EXAMPLE 1

In the reactions shown below dipic acid was obtained from Sigma Chemical as earlier explained. It was converted to (NH$_4$)$_2$dipic by the following procedure. To a suspension of 1.00 g (6.0 mmol) of dipicolinic acid in 1 mL of water were added to 20 mL (a large excess) of concentrated aqueous ammonia. The mixture was heated at 60°-70° C. and dried without charring. The white residue was dissolved in 5 mL of water and dried again at 60°-70° C. This procedure was repeated six times in order to remove NH$_3$ completely. Yield, 1.10 g or 91%. Proton NMR spectrum ($\delta$ values) in D$_2$O: 8.62, t; 8.41, d; $^3$J(H—H)=7.8 Hz.

Where K$_2$dipic was used it was prepared in the following procedure. A solution containing 0.109 g (0.65 mmol) of dipicolinic acid and 0.071 g (1.27 mmol) of KOH in 3 mL of water was dried at 60°-70° C. to yield a white residue. An excess of base was avoided lest it might cause unwanted side reactions with Pt complexes in subsequent experiments. Proton NMR spectrum ($\delta$ values) in D$_2$O: 8.18, t; 8.10, d; $^3$J(H—H)=7.6 Hz.

The thermochromic complex was prepared in the following manner. A solution containing 0.402 g (2.0 mmol) of (NH$_4$)$_2$dipic in 40 mL of water was added dropwise to a stirred solution containing 0.830 g (2.0 mmol) of K$_2$[PtCl$_4$] in 10 mL of water. The reaction is best carried out in the dark, or in dilute (ca. 0.25 M) HCl instead of water, in order to minimize formation of platinum metal and other side reactions. The mixture was heated at 80° C. for 4 h and its color changed from red to orange. The UV band at 272 nm, due to the free dipicolinate anion, decreased while a broad one at ca. 330 nm, due to the chelate complex, increased. The orange reaction mixture was cooled to room temperature and the NH$_4^+$ ions replaced with K$^+$ ions on a column of CM 52 cation exchanger, sized 2.5×14 cm, that had been equilibrated with 0.10 M KCl. The same KCl solution was used as an eluent. Two bands formed. The first one was red and contained the unspent K$_2$[PtCl$_4$]; the second one was yellow and contained K[Pt(dipic)Cl]. The yellow solution was concentrated in a rotary evaporator and the red or orange solid that formed was filtered off, washed with ethanol and acetone, and dried in a desiccator. The average weight of the first crop from several syntheses was 0.30 g; the yield (36%) was sacrificed for the sake of purity. Anal. Found (calcd. for C$_7$H$_3$NO$_4$ClKPt): C, 19.31 (19.34); H, 0.99 (0.70); N, 3.12 (3.22). (All elemental analyses were done by Galbraith Laboratories, Inc.) Proton NMR spectrum ($\delta$ values) in D$_2$O: 8.45, t; 7.92, d; $^3$J(H—H)=8.0 Hz. Infrared bands (cm$^{-1}$) in Nujol mull were as follows. For the red salts: 3539 w, 3053 w, 2912 s, 1680 s mult, 1317 s mult, 1151 m, 1103 m, 914 w, 831 w, 770 m, 752 m, 675 m, 596 w, 462 m, 368 vw, 331 m, 219 m, and 300 m; for the orange salt: 3086 w, 3074 w, 2926 s, 1668 s mult, 1323 s, 1150 m, 1136 m, 1111 m, 1106 m, 916 w, 831 w, 768 m, 752 m, 675 m, 599 w, 463 m, 457 m, 370 vw, 332 m, 332 m, 301 m, 263 vw, 247 vw, and 223 vw.

EXAMPLES 2-8

Salts: M [Pt(dipic)Cl]$_z$: The cations K$^+$ and NH$_4^+$, which accompany [Pt(dipic)Cl]$^-$ in the orange reaction mixture, were replaced with Li$^+$, Na$^+$, Cs$^+$, Mg$^{2+}$, Ca$^{2+}$, Ba$^{2+}$, and Al$^{3+}$ on columns of Amberlite CG-52 cation exchanger resin that were previously equilibrated with 0.10 M solutions of the corresponding Cl$^-$ or NO$_3^-$ salts and washed with water. The amount of the resin used was greater than that required by the resin capacity and the quantities of the cations in solution. Elution with the equilibrating solution in each case produced the red band of the unspent K$_2$[PtCl$_4$], which moved first, and the yellow one of the [Pt(dipic)Cl]$^-$ salt, which moved second. Only the yellow band was collected.

All the salts above, with the exception of the sodium and calcium salts that precipitated rather than formed a polymeric gel, yield pale yellow solutions in water. When the yellow solution was cooled, but well above the freezing point, it turned to the gel-like substance. This substances was examined and found to actually be polymeric and microcrystalline in structure. At the beginning of the thermochromic transition, red spots appear in the yellow solution; on further cooling at moderate rates, approximately 10 to 20 degrees Celsius per minute, the red spots grow and merge rapidly until the former solution becomes an immobile, although not frozen, mass. All of the transformations were observed to be reversible on heating. Although, as illustrated in FIG. 1, the color change occurs over a temperature range with some hysteresis, the thermochromic transition can be classified as sudden.

Variation of the solution concentration, again as illustrated in FIG. 1, at constant temperature causes the same color change as variation of its temperature at constant concentration. When the yellow aqueous solution is concentrated by evaporation, it suddenly turns into the same red gel-like substance as when it is cooled. Correspondingly when the red substance is added to water it gives a yellow solution, even at the same temperature. Evidently the color change can be effected by either vertical or horizontal transitions in the phase diagram shown in FIG. 1. Some studies with different buffers spanning the pH range of from 2 to 9.6 were conducted. These qualitative experiments permitted the general conclusion that the thermochromic transition and the phase change occur in the weakly acid and neutral solution alike. Moreover, it was observed that the platinum(II) complex is unaffected by the presence of other ions. In particular, the solution of the pure complex and the reaction mixture (which also contained ammonium, chloride and tetrachloroplatnate ions) behaved identically upon heating and cooling and gave similar diagrams of the type shown in FIG. 1. It is also clear from experiments that the thermochromism occurs only in solvents that are mostly aqueous in composition.

Finally, as illustrated in FIG. 1, since the change between the red and yellow forms occurs over a relatively narrow temperature range, and since this range can be set simply by adjusting the concentration of the solution, the platinum(II) complex salts of this invention promise to be excellent temperature indicators. They may be especially useful in applications when deviations from a certain "alert temperature" must be detected quickly. Such examples may include packaging objects of art, where the packaged products are highly temperature-sensitive; storage of perishable foods; control of workplaces and of other enclosed areas; etc. It therefore can be seen that the invention accomplishes at least all of its stated objectives.

What is claimed is:

1. Thermochromic platinum(II) complexes of the formula:

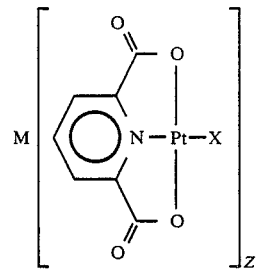

wherein M is a cation, X is a halide ion, and Z is a whole number equal to the positive charge of M.

2. The complexes of claim 1 wherein M is monovalent.

3. The complexes of claim 1 wherein M is divalent.

4. The complexes of claim 1 wherein M is trivalent.

5. The complexes of claim 1 wherein X is chloride.

6. The complexes of claim 1 wherein X is bromide.

7. The complexes of claim 1 wherein X is iodide.

8. The complexes of claim 1 wherein M is selected from the group consisting of hydrogen, lithium, sodium, cesium, ammonium, magnesium, barium, and aluminum.

9. Thermochromatic compositions which comprise an aqueous solution of a platinum(II) complex of the formula:

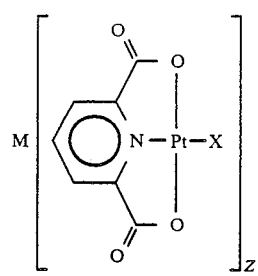
wherein M is a cation, X is a halide ion, and Z is a whole number equal to the positive charge of M.
10. The compounds of claim 9 whose concentration in aqueous solution is from 5 mM to 200 mM.
11. The composition of claim 9 wherein the concentration of said aqueous solution is from 10 mM percent to 60 mM percent.
* * * * *